United States Patent [19]
Ali

[11] Patent Number: 6,037,343
[45] Date of Patent: Mar. 14, 2000

[54] FIBRINOGEN RECEPTOR ANTAGONISTS

[75] Inventor: Fadia El-Fehail Ali, Cherry Hill, N.J.

[73] Assignee: Smithkline Beecham Corporation, Philadelphia, Pa.

[21] Appl. No.: 08/875,356

[22] PCT Filed: Dec. 22, 1995

[86] PCT No.: PCT/US95/16963

§ 371 Date: Dec. 22, 1995

§ 102(e) Date: Dec. 22, 1995

[87] PCT Pub. No.: WO96/19223

PCT Pub. Date: Jun. 27, 1996

[51] Int. Cl.$^7$ .............. A61K 31/495; A61K 31/445; C07D 211/08; C07D 401/02; C07D 211/30; C07D 213/02; C07D 413/02

[52] U.S. Cl. .......... 514/252; 514/316; 514/318; 514/340; 544/360; 546/189; 546/191; 546/194; 546/274

[58] Field of Search .............. 514/252, 316, 514/318, 340; 544/360; 546/189, 191, 194, 274

[56] References Cited

U.S. PATENT DOCUMENTS

| | | | |
|---|---|---|---|
| 5,039,805 | 8/1991 | Alig et al. | 546/244 |
| 5,084,466 | 1/1992 | Alig et al. | 514/353 |
| 5,292,756 | 3/1994 | Duggan et al. | 514/331 |
| 5,648,368 | 7/1997 | Egbertson et al. | 514/331 |
| 5,814,636 | 9/1998 | Katano et al. | 514/252 |
| 5,922,717 | 7/1999 | Pieper et al. | 514/252 |

FOREIGN PATENT DOCUMENTS

WO 96/19222  6/1996  WIPO.

*Primary Examiner*—Jose' G. Dees
*Assistant Examiner*—Sabiha N. Qazi
*Attorney, Agent, or Firm*—Zoltan Kerekes; Stephen Venetianer; Charles M Kinzig

[57] ABSTRACT

This invention relates to compound of formula (I) which are effective for inhibiting platelet aggregation, pharmaceutical compositions for effecting such activity, and a method for inhibiting platelet aggregation.

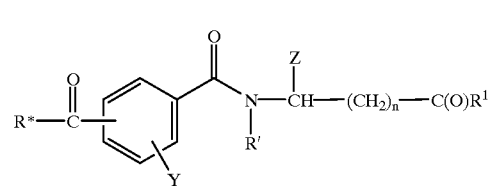

17 Claims, No Drawings

FIBRINOGEN RECEPTOR ANTAGONISTS

FIELD OF THE INVENTION

This invention relates to novel compounds which inhibit platelet aggregation, pharmaceutical compositions containing the compounds and methods of using the compounds.

BACKGROUND OF THE INVENTION

Platelet aggregation is believed to be mediated primarily through the fibrinogen receptor, or GPIIb-IIIa platelet receptor complex, which is a member of a family of adhesion receptors referred to as integrins. It has been found that frequently the natural ligands of integrin receptors are proteins which contain an Arg-Gly-Asp sequence. Von Willebrand factor and fibrinogen, which are considered to be natural ligands for the GPIIb-IIIa receptor, possess and Arg-Gly-Asp (RGD in single letter amino acid code) sequence in their primary structure. Functionally, these proteins are able to bind and crosslink (GPIIb-IIIa receptors on adjacent platelets and thereby effect aggregation of platelets.

Fibronectin, vitronectin and thrombospondin are RGD-containing proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Linear and cyclic peptides which bind to vitronectin and contain an RGD sequence are disclosed in WO 89/05150 (PCT US88/04403). EP 0 275 748 discloses linear tetra- to hexapeptides and cyclic hexa- to octapeptides which bind to the GPIIb-IIIa receptor and inhibit platelet aggregation. Other linear and cyclic peptides, the disclosure of which are incorporated herein by reference, are reported in EP-A 0 341 915. However, the peptide like structures of such inhibitors often pose problems, such as in drug delivery, metabolic stability and selectivity. Inhibitors of the fibrinogen receptor which are not constructed of natural amino acid sequences are disclosed in EP-A 0 372,486, EP-A 0 381 033 and EP-A 0 478 363. WO 92/07568 (PCT/US91/08166) discloses fibrinogen receptor antagonists which mimic a conformational γ-turn in the RGD sequence by forming a monocyclic seven-membered ring structure. There remains a need, however, for novel fibrinogen receptor antagonists (e.g., inhibitors of the GPIIb-IIIa protein) which have potent in vivo and in vitro effects and lack the peptide backbone structure of amino acid sequences.

The present invention discloses novel compounds. These compounds inhibit the GPIIb-IIIa receptor and inhibit platelet aggregation.

SUMMARY OF THE INVENTION

In one aspect this invention is a compound as described hereinafter in formula (I).

This invention is also a pharmaceutical composition for inhibiting platelet aggregation or clot formation, which comprises a compound of formula (I) and a pharmaceutically acceptable carrier.

This invention is further a method for inhibiting platelet aggregation in a mammal in need thereof, which comprises internally administering an effective amount of a compound of formula (I).

In another aspect, this invention provides a method for inhibiting reocclusion of an artery or vein in a mammal following fibrinolytic therapy, which comprises internally administering an effective amount of a fibrinolytic agent and a compound of formula (I). This invention is also a method for treating stroke, transient ischemia attacks, or myocardial infarction.

DETAILED DESCRIPTION OF THE INVENTION

This invention discloses compounds which inhibit platelet aggregation. The compounds of the instant invention are believed to interact favorably with the GPIIb-IIIa receptor.

Although not intending to be bound to any specific mechanism of action, these compounds are believed to inhibit the binding of fibrinogen to the platelet-bound fibrinogen receptor GPIIb-IIIa, and may interact with other adhesion proteins via antagonism of a putative RGD binding site.

The compounds of this invention are compounds of formula (I):

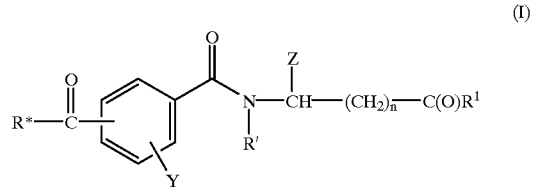

wherein:

R* is

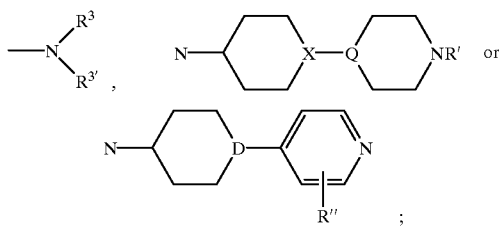

$R^1$ is OR' or NR'R';

each R' independently is hydrogen or $C_{1-6}$alkyl;

R'' is hydrogen, $C_{1-6}$alkyl, or NR'R';

X and Q independently are CH or N, with the proviso that X and Q are not simultaneously N;

D is CH or N, with the proviso that when D is N, R'' is NR'R';

Y is hydrogen, $C_{1-6}$alkyl, halo, $CF_3$, $CH_2OR^2$, $COR^2$, $CONR^2R^2$, $CO_2R^2$, CN, aryl, heteroaryl, $NR^2R^2$, $NR^2COR^2$, $NR^2CO_2R^2$, $NR^2CONR^2R^2$, $NR^2SO_2R^2$, $NO_2$, $OR^2$, $S(O)_{0-2}R^2$, or $SO_{(0-2)}CF_3$;

Z is hydrogen, $C_{1-6}$alkyl, $CH_2OR^2$, $CH_2CO_2R^2$, $C_{2-6}$alkenyl, $C_{2-6}$alkynyl, aryl, aralkyl$C_{1-6}$, heteroaryl, heteroaralkyl$C_{1-6}$, $COR^2$, $CONR^2R^2$, $CO_2R^2$, $NR^2R^2$, $NR^2COR^2$, $NR^2CONR^2R^2$, $NR^2CO_2R^2$, $NR^2SO_2R^2$, $OR^2$, $SO_2R^2$, or $SO_2NR^2R^2$;

$R^2$ is hydrogen, $C_{1-6}$alkyl, aralkyl$C_{1-6}$, aryl, heteroaralkyl$C_{1-6}$, or heteroaryl;

$R^3$ and $R^{3'}$ independently are —$(CH_2)_s$—Ⓝ;

Ⓝ is piperidine, piperazine, or 2-, 3-, or 4-pyridine;

s is 1–4; and n is 0–3;

or a pharmaceutically acceptable salt thereof.

Also included in this invention are pharmaceutically acceptable addition salts, complexes or prodrugs of the compounds of this invention. Prodrugs are considered to be any convalently bonded carriers which release the active parent drug according to formula (I) in vivo.

In cases wherein the compounds of this invention may have one or more chiral centers, unless specified, this invention includes each unique nonracemic compound which may be synthesized and resolved by conventional techniques. In cases in which the compounds have unsaturated double bonds, both the cis (Z) and trans (E) are within the scope of this invention. The meaning of any substituent at any one occurrence is independent of its meaning, or any other substituent's meaning, at any other occurrence, unless specified otherwise.

With reference to formula (I), compounds of formula (Ia) are preferred:

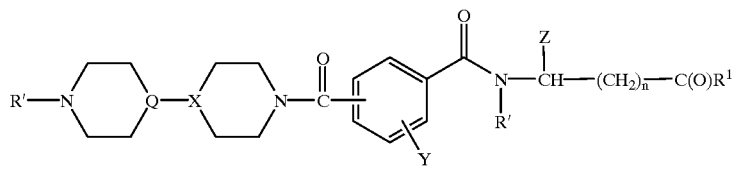

wherein:

$R^1$ is OR' or NR'R';

each R' independently is hydrogen or $C_{1-6}$alkyl;

X and Q independently are CH or N, with the proviso that X and Q are not simultaneously N;

Y is hydrogen, $C_{1-6}$alkyl, halo, $CF_3$, $CH_2OR^2$, $COR^2$, $CONR^2R^2$, $CO_2R^2$, CN, aryl, heteroaryl, $NR^2R^2$, $NR^2COR^2$, $NR^2CO_2R^2$, $NR^2CONR^2R^2$, $NR^2SO_2R^2$, $NO_2$, $OR^2$, $S(O)_{0-2}R^2$, or $SO_{(0-2)}CF_3$;

Z is hydrogen, $C_{1-6}$alkyl, $CH_2OR^2$, $CH_2CO_2R^2$, $C_{2-6}$alkenyl, $C_{2-6}$alkynyl, aryl, aralkyl$C_{1-6}$, heteroaryl, heteroaralkyl$C_{1-6}$, $COR^2$, $CONR^2R^2$, $CO_2R^2$, $NR^2R^2$, $NR^2COR^2$, $NR^2CONR^2R^2$, $NR^2CO_2R^2$, $NR^2SO_2R^2$, $OR^2$, $SO_2R^2$, or $SO_2NR^2R^2$;

$R^2$ is hydrogen, $C_{1-6}$alkyl, aralkyl$C_{1-6}$, aryl, heteroaralkyl$C_{1-6}$, or heteroaryl and;

n is 0–3;

or a pharmaceutically acceptable salt thereof.

Preferably, the compounds of formula (Ia) are those wherein Z is hydrogen, $C_{1-6}$alkyl, $CH_2OR^2$, $CH_2CO_2R^2$, $COR^2$, $CONR^2R^2$, $CO_2R^2$, $NR^2R^2$, or $OR^2$, $R^1$ is OR' and X and Q are each CH.

Preferred formula (Ia) compounds are:

N-[4,4'-bipiperidin-1-yl]isophthalyl-beta-alanine;
N-[4,4'-bipiperidin-1-yl]isophthalylglycine;
N-[4,4'-bipiperidin-1-yl]isophthalyl-4-aminobutyric acid; and
N-[4,4'-bipiperidin-1-yl]terephthalyl-beta-alanine;
or a pharmaceutically acceptable salt thereof.

With reference to formula (I), compounds of formula (Ib) are also preferred:

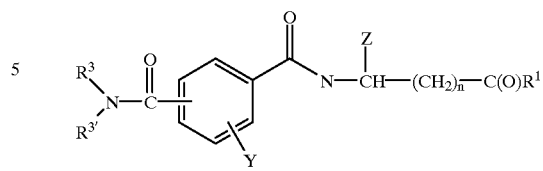

wherein:

$R^1$ is OR' or NR'R';

each R' independently is hydrogen or $C_{1-6}$alkyl;

Y is hydrogen, $C_{1-6}$alkyl, halo, $CF_3$, $CH_2OR^2$, $COR^2$, $CONR^2R^2$, $CO_2R^2$, CN, aryl, heteroaryl, $NR^2R^2$, $NR^2COR^2$, $NR^2CO_2R^2$, $NR^2CONR^2R^2$, $NR^2SO_2R^2$, $NO_2$, $OR^2$, $S(O)_{0-2}R^2$, or $SO_{(0-2)}CF_3$;

Z is hydrogen, $C_{1-6}$alkyl, $CH_2OR^2$, $CH_2CO_2R^2$, $C_{2-6}$alkenyl, $C_{2-6}$alkynyl, aryl, aralkyl$C_{1-6}$, heteroaryl, heteroaralkyl$C_{1-6}$, $COR^2$, $CONR^2R^2$, $CO_2R^2$, $NR^2R^2$, $NR^2COR^2$, $NR^2CONR^2R^2$, $NR^2CO_2R^2$, $NR^2SO_2R^2$, $OR^2$, $SO_2R^2$, or $SO_2NR^2R^2$;

$R^2$ is hydrogen, $C_{1-6}$alkyl, aralkyl$C_{1-6}$, aryl, heteroaralkyl$C_{1-6}$, or heteroaryl;

$R^3$ and $R^{3'}$ independently are —$(CH_2)_s$—Ⓝ;

Ⓝ is piperidine, piperazine, or 2-, 3-, or 4-pyridine;

s is 1–4; and n is 0–3;

or a pharmaceutically acceptable salt thereof.

Preferably, the compounds of formula (Ib) are those wherein Z is hydrogen, $C_{1-6}$alkyl, $CH_2OR^2$, $CH_2CO_2R^2$, $COR^2$, $CONR^2R^2$, $CO_2R^2$, $NR^2R^2$, or $OR^2$ and $R^1$ is OR'.

Preferred formula I(b) compounds are:

N-[[bis-4-(pyridyl)ethyl]amino]isophthalyl-beta-alanine;
N-{[bis-4-(piperidinyl)ethyl]amino}isophthalyl-beta-alanine;
N-{[bis-4-(pyridyl)ethyl]amino}terephthalyl-beta-alanine; and
N-[[bis-4-(piperidinyl)ethyl]amino]terephthalyl-beta-alanine;

or a pharmaceutically acceptable salt thereof.

With reference to formula (I), compounds of formula (Ic) are also preferred:

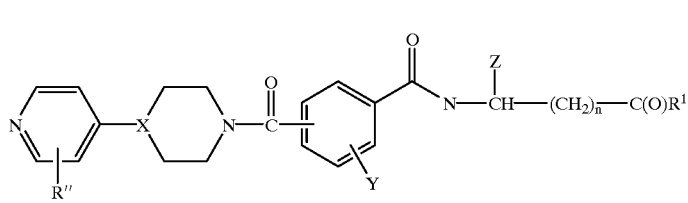

(Ic)

wherein:

$R^1$ is OR' or NR'R';

each R' independently is hydrogen or $C_{1-6}$alkyl;

R" is hydrogen, $C_{1-6}$alkyl, or NR'R';

X is CH or N;

Y is hydrogen, $C_{1-6}$alkyl, halo, $CF_3$, $CH_2OR^2$, $COR^2$, $CONR^2R^2$, $CO_2R^2$, CN, aryl, heteroaryl, $NR^2R^2$, $NR^2COR^2$, $NR^2CO_2R^2$, $NR^2CONR^2R^2$, $NR^2SO_2R^2$, $NO_2$, $OR^2$, $S(O)_{0-2}R^2$, or $SO_{(0-2)}CF_3$;

Z is hydrogen, $C_{1-6}$alkyl, $CH_2OR^2$, $CH_2CO_2R^2$, $C_{2-6}$alkenyl, $C_{2-6}$alkynyl, aryl, aralkyl$C_{1-6}$, heteroaryl, heteroaralkyl$C_{1-6}$, $COR^2$, $CONR^2R^2$, $CO_2R^2$, $NR^2R^2$, $NR^2COR^2$, $NR^2CONR^2R^2$, $NR^2CO_2R^2$, $NR^2SO_2R^2$, $OR^2$, $SO_2R^2$, or $SO_2NR^2R^2$;

$R^2$ is hydrogen, $C_{1-6}$alkyl, aralkyl$C_{1-6}$, aryl, heteroaralkyl$C_{1-6}$, or heteroaryl and;

n is 0–3;

or a pharmaceutically acceptable salt thereof.

Preferably, the compounds of formula (Ic) are those wherein Z is hydrogen, $C_{1-6}$alkyl, $CH_2OR^2$, $CH_2CO_2R^2$, $COR^2$, $CONR^2R^2$, $CO_2R^2$, $NR^2R^2$, or $OR^2$ and $R^1$ is OR', and X is N.

Preferred formula (Ib) compounds are:

N-[4-(4-pyridyl)piperazinyl]isophthalyl-beta-alanine; and
N-[4-(4-pyridyl)piperazinyl]terphthalyl-beta-alanine;

or a pharmaceutically acceptable salt thereof.

In the above description, $C_{1-6}$alkyl is meant to include methyl, ethyl, n-propyl, ispropyl, n-butyl, isobutyl, t-butyl, n-pentyl, isopentyl, neopentyl and hexyl and the simple aliphatic isomers thereof.

$C_{2-6}$ alkenyl as applied herein means an alkyl group of 2 to 6 carbons wherein a carbon-carbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included.

$C_{2-6}$ alkynyl means an alkyl group of 2 to 6 carbons wherein one carbon-carbon single bond is replaced by a carbon-carbon triple bond. $C_{2-6}$ alkynyl includes acetylene, 1-propyne, 2-propyne, 1-butyne, 2-butyne, 3-butyne and the simple isomers of pentyne and hexyne.

Aryl, as applied herein, means phenyl or naphthyl, or phenyl or naphthyl substituted by one to three moieties $R^{11}$. In particular, $R^{11}$ may be $C_{1-4}$alkyl, $C_{1-4}$alkoxy, $C_{1-4}$alkthio, trifluoroalkyl, OH, F, Cl, Br or I. Aralkyl$C_{1-6}$, as used herein, means an aryl group attached to a $C_{1-6}$alkyl chain.

Heteroaryl indicates an optionally substituted five or six membered aromatic monocyclic ring, or a nine or ten-membered bicyclic ring containing one to three heteroatoms chosen from the group of nitrogen, oxygen and sulfur, which are stable and available by conventional chemical synthesis. Illustrative heteroaryls are benzofuryl, benzimidazole, benzothiophene, furan, imidazole, and pyridine. Any accessible combination of up to three substituents, such as chosen from $R^{11}$, on the heteroaryl ring that is available by chemical synthesis and is stable is within the scope of this invention. Heteroaralkyl$C_{1-6}$, as used herein, means a heteroaryl group attached to $C_{1-6}$alkyl chain.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-6}$alkyl, Nph refers to 1- or 2-naphthyl and cHex refers to cyclohexyl. MeArg is $N^{\alpha}$-methyl arginine. Tet refers to 5-tetrazolyl.

Certain reagents are abbreviated herein. DCC refers to dicyclohexylcarbodiimide, DMAP refers to dimethylaminopyridine, DIEA refers to diisopropylethyl amine, EDC refers to N-ethyl-N'(dimethylaminopropyl) carbodiimide. HOBt refers to 1-hydroxybenzotriazole, THF refers to tetrahydrofuran, DMF refers to dimethyl formamide, NBS refers to N-bromosuccinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of the formula (II) with a compound of the formula (III):

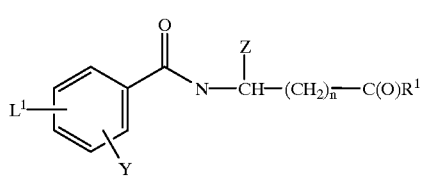

(II)

(III)

$L^2$—R* wherein Y, A, Z, n, $R^1$, and R* are defined in formula (I), with any reactive functional groups protected;

and thereafter removing any protecting groups, and optionally forming a pharmaceutically acceptable salt.

It will be apparent that the precise identity of $L^1$ in formula (II) is a functional group capable of reacting with $L^2$ of formula (III) to form the NCO linkage. For example, $L^1$ may be $CO_2H$ and the NCO linkage is obtained by activation of the carboxyl and condensation with (III) to give the desired amide. Methods for activating a carboxylic acid for condensation with an amide include treatment with a carbodiimide, with thionyl chloride for form an acid chloride, or with acid anhydrides, acid chlorides or chloroformates to form mixed anhydrides.

In another approach, $L^1$ may be bromo, iodo, trifluoromethylsulfonyloxy, etc. and the NCO linkage is formed by palladium-catalyzed aminocarbonylation with of (II) with (III) and carbon monoxide in a suitable solvent such as dimethylformamide, N-methylpyrrolidinone, toluene, etc.

Many additional methods for converting a carboxylic acid to an amide are known, and can be found in the art including standard reference books, such as "Compendium of Organic Synthetic Methods", Vol. I–VI (Wiley-Interscience).

Compounds of formula (I) are prepared by methods analogous to those described in Scheme I.

Scheme I

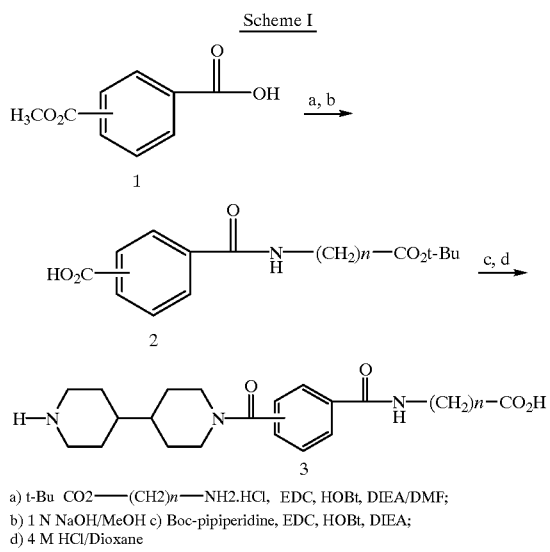

a) t-Bu CO2——(CH2)n——NH2.HCl, EDC, HOBt, DIEA/DMF;
b) 1 N NaOH/MeOH c) Boc-pipiperidine, EDC, HOBt, DIEA;
d) 4 M HCl/Dioxane The monomethylisophthalate (I-1) was condensed with t-butyl-β-alanine ester hydrochloride in the presence of DIEA, HOBt, H₂O and EDC in anhydrous DMF. Saponification of the resulting methyl ester with 1 N NaOH afforded the monoacid (I-2). Condensation of (I-2) with t-Boc-piperidine (prepared by the method described by Bondinell et. al. WO 94/14776) in the presence of EDC, HOBt. H₂O and DIEA afforded the fully protected version of (I-3). Simultaneous removing of the t-butyl ester and the N protected t-Boc group with 4 M HCl/dioxane afforded the final product (I-3) as its hydrochloride salt.

Coupling reagents as used herein denote reagents which may be used to form amide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to formamide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.*, 29, 984 (1986) and *J. Med. Chem.*, 30, 2291 (1987) are generally illustrative of the technique and are incorporated herein by reference.

Solution synthesis for the formulation of amide bonds is accomplished using conventional methods used to form amide bonds. Typically, the amine or aniline is coupled via its free amino group to an appropriate carboxylic acis substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitable protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran (THF), in the presence of a base, such as N-methyl morpholine, DMAP or a trialkylamine, with isobutyl chloroformate to form the "activated anhydride", which is subsequently reacted with the free amine of a second protected amino acid or aniline.

The reactive functional groups of the sidechains of each synthetic fragment are suitable protected as known in the art. Suitable protective groups are disclosed in Greene, PROTECTIVE GROUPS IN ORGANIC CHEMISTRY, John Wiley and Sons, New York, 1981. For example, the Boc, Cbz, phthaloyl or Fmoc group may be used for protection of an amino or amidino group. The Boc group is generally preferred for protection of an α-amino group. A t-Bu, cHex or benzyl ester may be used for the protection of the side chain carboxyl. A benzyl group or suitably substituted benzyl group (e.g., 4-methoxy-benzyl or 2,4-dimethoxy-benzyl) is used to protect the mercapto group or the hydroxyl group. A suitably substituted carbobenzyloxy group or benzyl group may be also used for the hydroxyl group or amino group. Suitable substitution of the carbobenzyloxy or benzyl protecting groups is ortho and/or para substitution with chloro, bromo, nitro or methyl, and is used to modify the reactivity of the protective group. Except for the Boc group, the protective groups for the amino moiety are, most conveniently, those which are not removed by mild acid treatment. These protective groups are removed by such methods as catalytic hydrogenation, sodium in liquid ammonia or HF treatment, as known in the art.

Acid addition salts of the compounds of this invention are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li+, Na+, K+, Ca++, Mg++ and NH₄+ are specific examples of cations present in pharmaceutically acceptable salts.

This invention provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, the compounds of this invention may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds of this invention may be used in vitro to inhibit the aggregation of platelets in blood and blood products, e.g., for storage, or for ex vivo manipulations such as in diagnostic or research use. This invention also provides a method of inhibiting platelet aggregation and clot formation in a mammal, especially a human, which comprises the internal administration of a compound of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venon and immune diseases, are likely to be responsive to such treatment. In addition, the compounds of this invention may be useful in a method for the prevention of metastatic conditions, the prevention or treatment of fungal or bacterial infection, inducing the immunostimulation, treatment of sickle cell disease, and the prevention or treatment of diseases in which bone resorption is a factor.

The compounds of formula (I) are administered either orally or parenterally to the patient, in a manner such that the concentration of drug in the plasma is sufficient to inhibit platelet aggregation, or other such indication. The pharmaceutical composition containing the compound is administered at a dose between about 0.2 to about 50 mg/kg in a manner consistent with the condition of the patient. For acute therapy, parenteral administration is preferred. For persistent states of hyperaggregability, an intravenous infusion of the peptide in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The compound of this invention is administered one to four times daily at a level of about 0.4 to about 50 mg/kg to achieve a total daily dose of about 0.4 to about 200 mg/kg/day.

This invention further provides a method for inhibiting the reocclusion of an artery or vein following fibrinolytic therapy, which comprises internal administration of a compound of formula (I) and a fibrinolytic agent. It has been found that administration of an peptide in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding a molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334. Other variants include hybrid proteins, such as those disclosed in EP 0 028 489, EP 0 155 387 and EP 0 297 882, all of which are incorporated herein by reference. Anistreplase is preferred hybrid protein for use in this invention. Fibrinolytic agents may be isolated from natural sources, but are commonly produced by traditional methods of generic engineering.

Useful formulations of tPA, SK, UK and pUK are disclosed, for example in EP-A 0 211 592, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compound of formula (I) and fibrinolytic in the same container, but formation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The compound of formula (I) is administered just prior to, at the same time as, or just after parenteral administration of tPA or other fibrinolytic agent. It may prove desirable to continue treatment with the peptide for a period of time well after reperfusion has been established to maximally inhibit post-therapy reocclusion. The effective dose of tPA, SK, UK or pUK may be from 0.5 to 5 mg/kg and the effective dose of the compound of this invention may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of the peptide inhibitor followed by an infusion of the fibrinolytic agent.

The pharmacological activity of the compounds of this invention is assessed by their ability to inhibit the binding of $^3$H-SK&F 107260, and known RGD-fibrinogen antagonist, to the GPIIbIIIa receptor; their ability to inhibit platelet aggregation, in vitro, and their ability to inhibit thrombus formation in vivo.

Inhibition of RGD-Mediated GPIIb-IIIa Binding
Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM $CaCl_2$ at 4° C. for 2 h. The lysate was centrifuged at 100,000 g for 1 h. The supernatant obtained was applied to a 5 mL lentil lectin sepharose 4B column (E. Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.
Incorporation of GPIIb-IIIa in Liposomes.

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70° C. until needed.
Competitive Binding to GPIIb-IIIa The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 μg/mL polylysine (Sigma Chemical Co., St. Louis, Mo.) at room temperature for 1 h to block nonspecific binding. Various concentrations of unlabeled benzadiazapines were added to the wells in quadruplicate. [$^3$H]-SK&F-107260 was applied to each well at a final concentration of 4.5 nM, followed by the addition of 1 μg of the purified platelet GPIIb-IIIa containing liposomes. The mixtures were incubated for 1 h at room temperature. The GBIIb-IIIa bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 μM unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: $Ki=IC50/(1+L/Kd)$, where L is the concentration of [3H]-SK&F-107260 used in the competitive binding assay (4.5 nM), and Kd is the dissociation constant of [3H]-SK&F-107260 which is 4.5 nM as determined by Scatchard analysis. The compounds of this invention inhibit [3H]-SK&F-107260 binding with a Ki in the range of about 0.1 micromolar to about 10.0 micromolar.

Inhibition of Platelet Aggregation

Inhibition of platelet aggregation was determined following the procedure described in Nichols, et a., *Thrombosis Research*, 75, 143 (1994). Blood was drawn from the antecubital vein of normal human volunteers who had not taken a cyclooxygenase inhibitor within the previous 14 days into a plastic syringe containing one part 3.8% trisodium citrate to nine parts blood. Platelet rich plasma was prepared by centrifuging the blood at 200 g for 10 min at RT. The platelet rich plasma was drawn off and the remaining blood was centrifuged at 2400 g for 5 min at RT to make platelet poor plasma. Platelet count was measured with a model ZB1 Coulter Counter (Coulter Electronics Inc., Hialeah, Fla.) and was adjusted to 300,000/μl using platelet poor plasma. Platelet aggregation was studied in a Chrono-Log model 400VS Lumi Aggregometer (Chrono-Log, Havertown, Pa.) using platelet rich plasma stirred at 1200 r.p.m. and maintained at 37° C., with platelet poor plasma as the 100% transmission standard. Concentration-response curves for the ability of compounds to inhibit platelet aggregation, measured as the maximum change in light transmission, induced by a maximal concentration of adenosine diphosphate (10 μM) were constructed and the $IC_{50}$ was determined as the concentration of antagonist required to produce 50% inhibition of the response to the agonist.

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629 (1980).

General

Nuclear magnetic resonance spectra were recorded at 400 MHz using a Bruker AC 400 spectrometer. CDCl$_3$ is deuteriochloroform, DMSO-d$_6$ is hexadeuteriodimethylsulfoxide, and CD$_3$OD is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromagographic support. 5 μ Apex-ODS indicates an octadecylsilyl derivatized silica gel chromatographic support having a nominal particle size of 5 μ, made by Jones Chromatography, Littleton, Colo. YMC ODS-AQ® is an ODS chromatographic support and is a registered trademark of YMC Co. Ltd. Kyoto, Japan. PRP-1® is a polymeric (styrene-divinylbenzene) chromatographic support, and is a registered trademark of Hamilton, Co., Reno, Nev. Celite® is a filter aid composed of acid-washed diatomaceous silica, and is a registered trademark of Manville Corp., Denver, Colo.

Monomethyl isophthalate, monomethylterephthalate, tert-butyl-β-alanine hydrochloride and t-butyl glycinate hydrochloride were purchased from Aldrich, Lancaster chemicals or Bachem, 4-pyridyl piperazine was purchased from EMK-CHEMIE GMBH and N-(tert-butoxycarbonyl)-4,4'-bipiperidine was prepared by the method of Bondinell, et al., WO 94/14776.

EXAMPLE 1

Preparation of N-[4,4'-Bipiperidin-1-yl]isophthalyl-beta-alanine hydrochloride a) N-(methylisophthalyl)-beta-alanine-tert-butyl ester 1-(3-Dimethylaminopropyl)-3-ethylcarbodiimide hydrochloride (EDC) (11.60 g, 60.5 mmol) was added to a solution of monomethyl isophthalate (9.91 g, 55 mmol), tert-butyl-β-alanine hydrochloride (9.99 g, 55 mmol), 1-hydroxybezotriazole hydrate (HOBt.H$_2$O), (8.18 g, 60.5 mmol) and diisopropylethylamine (DIEA), (21.1 mL, 121 mmol) in anhydrous DMF (50 mL) at RT. After stirring for 20 hr, the reaction mixture was concentrated on rotavap (high vacuum). The residue was taken into ethyl acetate (EtOAc) and washed successively with H$_2$O (3×100 mL), 5% citric acid (3×100 ml), H$_2$O (3×100 mL), 10% Na$_2$CO$_3$ (2×100 mL), H$_2$O (3×100 mL) and finally once with saturated salt solution (NaCl). The organic extract was dried (anhydrous MgSO$_4$), filtered and concentrated and chromatography (silica gel 1% methanol/methylene chloride) to yield the title compound (13.6 g, 81%) as a white solid. $^1$H NMR (400 MHz, CDCl$_3$) δ 8.38 (s, 1 H), 8.18 (d, 1 H), 8.01 (d, 1 H), 7.53 (t, 1 H), 3.94 (s, 3 H), 3.71 (m, 2 H), 2.57 (t, 2 H), 1.47 (s, 9 H). MS (ES) m/e 308 [M+H]$^+$.

b) N-(carboxyisophthalyl)-beta-alanine-tert-butyl ester

A solution of 1N NaOH (88.7 mL, 88.7 mmol) was added dropwise to a solution of the compound of Example 1 (a) (13 g, 42.3 mmol) in MeOH (120 mL). The resulting solution was stirred at RT for 20 h. It was then concentrated, and the resulting oily residue was dissolved in H$_2$O (30 mL) and acidified upon cooling with 6 M HCl to acidic pH to afford a white precipitate. The solid was filtered, washed with water and dried under vacuum to yield the title compound (4.75 g, 38.3% yield) as a white solid: $^1$H NMR (400 MHz, DMSO-d$_6$) δ 8.73 (br, 1 H), 8.40 (s, 1 H), 8.06 (dd, 2 H), 7.59 (t, 1 H), 3.46 (m, 2 H), 2.49 (m, 2H), 1.38 (s, 9H); MS (ES) m/e 294 [M+H]$^+$.

c) N-[(tert-butoxycarbonyl)-4,4'-bipiperidinyl]isophthalyl-beta-alanine-tert-butylester EDC (708 mg, 3.9 mmol) was added to a solution of the compound of Example 1 (b) (879 mg, 3.0 mmol), tert-butoxycarbonyl)-4,4'-bipiperidin (805 mg, 3 mmol) and DIEA (1.05 mL, 6 mmol) in anhydrous DMF (2 mL) at RT. After stirring for 20 h, the reaction was concentrated on rotavap (high vacuum). The resulting residue was taken into EtOAc and washed successively with H$_2$O (3×20 mL), 5% citric acid (3×20 ml), H$_2$O, 10% Na$_2$CO$_3$ (3×20 ml) and saturated NaCl. The organic extract was dried (anhydrous MgSO$_4$), filtered, concentrated and chromatographed (silica gel 1.5% methanol/methylene chloride) to yield the title compound (810 m g, 36%) as a white solid. $^1$H NMR (400 MHz, CDCl$_3$) δ 7.78 (s, 1H), 7.51–7.48 (dd, 2H), 6.90 (t, 1H), 4.11–1.16 (m, 4H); MS (ES) m/e 544.4 [M+H]$^+$.

d) N-[4,4'-Bipiperidin-1-yl]isophthalyl-beta-alanine hydrochloride

To a solution of the compound of Example 1 (c) (560 mg, 1.03 mmol) in CH$_2$Cl$_2$ (12 ml) was added 4 M HCl/dioxane (12 ml, 48 mmol) at Rt. The resulting mixture was stirred for 22 h. The resulting white precipitate was collected by filtration to yield the title compound (300 mg, 75%) as a white solid. HPLC k' 8.46 (Ultrasphere ® ODS, gradient, A:acetonitrile B:water-0.1% trifluoroacetic acid, 5–60% acetonitrile during 20 min; UV detection at 220 nm). $^1$H NMR (400 MHz, DMSO-d$_6$) δ 8.82 (br, 1H), 8.64 (t, 1H), 7.91 (d, 1H), 7.82 (s, 1H), 7.52 (d, 1H), 7.51 (s, 1H), 3.46–1.10 (m, 22H). MS (ES) m/e 388.2 [M+H]$^+$; Anal. (C$_{21}$H$_{29}$N$_3$O$_4$ . 2HCl . 2 H$_2$O) calcd: C, 50.81; H, 7.11; N, 8.46. Found: C, 50.97; H, 7.25; N, 8.44.

EXAMPLE 2

Preparation of N-[[Bis-4-(pyridyl)ethyl]amino]isophthalyl-beta-alanine hydrochloride a) Bis (4-pyridylethyl) amine A mixture or 4-vinyl pyridine (10.0 g, 95.1 mmol) and ammonium chloride (5.1 g, 95.1 mmol) was heated to reflux in MeOH (90 ml) under argon for 27 h. The resulting precipitate was filtered and the filtrate was concentrated on rotavap. The resulting residue was dissolved in H$_2$O (200 ml) and basified with 2N NaOH to pH 10.5 and extracted with CH$_2$Cl$_2$ (3×100 ml). The Combined organic extracts were dried (anhydrous MgSO$_4$) and concentrated to a yellow oil which was purified by column chromatography on silica gel (10% MeOH/CH$_2$Cl$_2$) to yield the title compound (4.0 g, 18.5%) as a yellow solid: $^1$H NMR (400 MHz, DMSO-d$_6$) δ 8.50 (d, 4H), 7.10 (d, 4H), 2.93 (t, 4H), 2.80 (t, 4H), 1.81 (br. 1H); MS (ES) m/e 228.2 [M+H]$^+$.

b) N-[[Bis-4-(pyridyl)ethyl]amino]isophthalyl-beta-alanine-tert-butylester

Following the procedure of Example 1 (c), EDC (421 mg, 2.2 mmol) was added to a solution of the compound of Example 1 (b) (586 mg, 2.0 mmol), bis-4-(pyridylethyl) amine (454 mg, 2.0 mmol), HOB:t $H_2O$ (297 m g, 2.2 mmol) and DIEA (0.42 mL, 2.4 mmol) in anhydrous DMF (5 mL) at RT. After stirring for 20 h, the reaction mixture was concentrated on rotavap (high vacuum). The resulting residue was taken into EtOAc and washed with $H_2O$ (3×10 mL) and once with saturated NaCl. The organic extract was dried (anhydrous $MgSO_4$), filtered and concentrated. The resulting residue was purified, and silica gel chromatography (3% $MeOH/CH_2Cl_2$) to yield the title compound (330 mg, 33%) as a white solid. $^1H$ NMR (400 MHz, $CDCl_3$) δ 8.38 (s, 1 H), 8.18 (d, 1H), 8.01 (d, 1H), 7.53 (t, 1H), 3.94 (s, 3H), 3.71 (m, 2H), 2.57 (t, 2H), 1.47 (s, 9H).

c) N-[[Bis-4-(pyridyl)ethyl]amino]isophthalyl-beta-alanine hydrochloride

A solution of 4 M HCl/dioxane (10 ml, 40 mmol) was added dropwise to a solution of the compound of Example 2 (b) (450 mg, 0.89 mmol) in $CH_2Cl_2$ (10 ml) at RT. After stirring for 22 h, a white solid precipitated out, which was collected by filtration to yield the title compound (120 mg, 30%) as a white solid. HPLC k' 8.18 (Ultrasphere ® ODS, gradient, A:acetonitrile B:water-0.1% trifluoroacetic acid, 5–60% acetonitrile during 20 min; UV detection at 220 nm). $^1H$ NMR (400 MHz, DMSO-$d_6$) δ 8.52 (d, 2H), 8.38 (d, 2H), 7.85 (d, 1H), 7.63 (s, 1H), 7.45 (t, 1H), 7.36 (d, 2H), 7.18 (d, 1H), 6.97 (d, 2H), 3.74 (t, 2H), 3.45 (t, 2H), 2.97 (t, 4H), 2.78 (t, 4H). MS (ES) m/e 447.2 $[M+H]^+$. Anal. ($C_{25}H_{26}N_4O_4$ . 0.9 HCl) calcd: C, 62.65; H, 5.66; N, 11.69. Found: C, 62.61; H, 5.99; N, 11.42.

EXAMPLE 3

Preparation of N-{[Bis-4-(piperidinyl)ethyl]amino}isophthalyl-beta-alanine hydrochloride a) N-{[Bis-4-(piperidinyl)ethyl]amino}isophthalyl-beta-alanine-tert-butylester A mixture of the compound of Example 2 (b) (300 mg, 0.6 mmol), 4 M HCl/dioxane (2.0 ml) and $PtO_2$ (140 mg) was hydrogenated at 50 psi in a Parr apparatus at RT for 5 h. The reaction mixture was purged with argon, filtered and concentrated to yield the title compound (280 mg. 91%) as pale yellow solid. MS (ES) m/e 515.4 $[M+H]^+$.

b) N-{[Bis-4-(piperidinyl)ethyl]amino}isophthalyl-beta-alanine hydrochloride

Following the procedure of Example 2 (c), the compound of Example 3 (a) was treated with a solution of 4 M HCl/dioxane to yield the title compound (140 mg, 60%) as a white solid. HPLC k' 8.73 (Ultrasphere ® ODS, gradient, A:acetonitrile B:water-0.1% trifluoroacetic acid, 5–60% acetonitrile during 20 min; UV detection at 220 nm). $^1H$ NMR (400 MHz, DMSO-$d_6$) δ 8.42 (t, 1H), 7.9 2 (d, 1H), 7.84 (s, 1H), 7.52 (t, 1H), 7.44 (d, 1H), 3.47–1.27 (m, 32 H). MS ((ES) m/e 459.2 $[M+H]^+$. Anal. ($C_{25}H_{38}N_4O_4$. HCl . 2.25 $H_2O$) calcd: C, 56.06; H, 8.19; N, 10.46. Found: C, 55.95; H, 8.26; N, 10.42.

EXAMPLE 4

Preparation of N-[4,4'-Bipiperidin-1-yl]isophthalylglycine a) Methyl [N-(tert-butoxycarbonyl)-4,4'-bipiperidin-1-yl]isophthalate (EDC) (1.25 g, 6.5 mmol) was added to a solution of monomethyl isophthalate (0.9 g, 5 mmol), N-(tert-butoxycarbonyl)-4,4-bipiperidine hydrochloride (1.53 g, 5 mmol), HOBt. $H_2O$ (0.88 g, 6.5 mmol) and DIEA (1.75 mL, 10 mmol) in anhydrous DMF (25 mL) at RT. After stirring for 20 h, the reaction was concentrated on rotavap (high vacuum). The yellow oily residue was taken into EtOAc (100 mL) and washed successively with $H_2O$ (3×30 mL), 5% citric acid (3×30 ml), $H_2O$ (3×30 mL), 10% $Na_2CO_3$ (2×30 mL), $H_2O$ (3×30 mL) and finally once with saturated salt solution (NaCl). The organic extract was dried (anhydrous $Na_2SO_4$), filtered and concentrated to yield the title compound (2.0 g, 93%) as a white waxy material. HPLC k' 12.7 (Ultrasphere ® ODS, gradient, A:acetonitrile B:water-0.1% trifluoroacetic acid, 5–60% acetonitrile during 20 min; UV detection at 220 nm). $^1H$ NMR (400 MHz, $CDCl_3$) δ 8.08 (m, 1 H), 7.6 (m, 1 H), 7.4 (m, 1 H), 7.3 (s, 1 H), 3.94 (s, 3 H), 2.6 (m, 2 H), 1.65–1.1 (m, 16 H), 1.47 (s, 9 H). MS (ES) m/e 431.4 $[M+H]^+$.

b) [N-(tert-butoxycarbonyl)-4,4'-bipiperidin-1-yl]isophthalic acid

A solution of 1N NaOH (7 mL, 7 mmol) was added dropwise to a solution of the compound of Example 4 (a) (2.0 g, 4.65 mmol) in a 1:1 mixture of methanol-tetrahydrofuran (30 mL). The resulting solution was stirred at RT for 20 h. It was then concentrated, and the resulting oily residue was dissolved in $H_2O$ (30 mL) and acidified upon cooling with 50% acetic acid to acidic pH (5.0). The aqueous solution was then extracted with EtOAc, dried (anhydrous $Na_2SO_4$), filtered and concentrated to yield the title compound (1.73 g, 89%) as a white fluffy powder. HPLC k' 10.9 (Ultrasphere ® ODS, gradient, A:acetonitrile B:water-0.1% trifluoroacetic acid, 5–60% acetonitrile during 20 min; UV detection at 220 nm). MS (ES) m/e 417.2 $[M+H]^+$.

c) N-[(tert-butoxycarbonyl)-4,4'-bipiperidinyl]isophthalylglycine tert-butylester EDC (242 mg, 1.25 mmol) was added to a solution of the compound of Example 4 (b) (520 mg, 1.25 mmol), tert-butylglycine ester hydrochloride (210 mg, 1.25 mmol), HOBt. $H_2O$ (170 mg, 1.25 mmol) and DIEA (480 μL, 2.75 mmol) in anhydrous DMF (7 mL) at RT. After stirring for 20 h, the reaction was concentrated on rotavap (high vacuum). The resulting residue was taken into EtOAc and washed successively with $H_2O$ (3×20 mL), 5% citric acid (3×20 ml), $H_2O$, 10% $Na_2CO_3$ (3×20 ml) and saturated NaCl. The organic extract was dried (anhydrous $Na_2SO_4$), filtered and concentrated to yield the title compound (520 m g, 78%) as a white solid. HPLC k' 12.5 (Ultrasphere ® ODS, gradient, A:acetonitrile B:water-0.1% trifluoroacetic acid, 5–60% acetonitrile during 20 min; UV detection at 220 nm). MS (ES) m/e 530.4 $[M+H]^+$.

d) N-[4,4'-Bipiperidin-1-yl]isophthalylglycine

To a solution of the compound of Example 4 (c) (500 mg, 0.94 mmol) in $CH_2Cl_2$ (8 ml) was added trifluoroacetic acid (TFA) (2 ml) at Rt. The resulting mixture was stirred for 20 h, then it was concentrated to dryness on rotavap. The resulting residue was dissolved in water, and the pH was adjusted to 8 by means of dilute ammonium hydroxide. The aqueous solution was purified on flash ODS column (step gradient, 8–15% acetonitrile/water. The fractions containing the pure compound were collected, concentrated and lyophilized to yield the title compound (265 mg, 74%) as a white powder. HPLC k' 5.0 (Ultrasphere ® ODS, gradient, A:acetonitrile B:water-0.1% trifluoroacetic acid, 5–60% acetonitrile during 20 min; UV detection at 220 nm). $^1H$ NMR (400 MHz, DMSO-$d_6$/TFA) δ 9.0 (brt. 1H), 8.45 (br, 1H), 8.15 (brd, 1H), 7.95 (m, 1H), 7.9 (s, 1H), 7.55 (m, 1H), 4.6 (brm, 1H), 3.95 (d, 2H), 2.6–3.7 (m, 11 H), 1.1–1.9 (m, 11H). MS (ES) m/e 374.2 [M+H]$^+$; Anal. ($C_{20}H_{27}N_3O_4 \cdot 1.5$ $H_2O$) calcd: C, 59.98; H, 7.55; N, 10.45. Found: C, 59.70; H, 7.64; N, 10.49.

EXAMPLE 5

Preparation of N-[4-(4-pyridyl)piperazinyl] isophthalyl-beta-alanine a) N-[4-(4-pyridyl)piperazinyl]isophthalyl-beta-alanine-tert-butylester Following the procedure of Example 1 (c), a mixture containing compound of 1 (b) (330 mg, 1.13 mmol), EDC (238 mg, 1.24 mmol), HOBt. $H_2O$ (170 m g, 1.24 mmol), 1(4-pyridyl)-piperazine (184 m, 1.13 mmol), and diisopropylethylamine (0.24 mL, 1.36 mmol) in anhydrous DMF (5 mL) at RT were stirred for 20 h. The reaction was then concentrated on the rotavap (high vacuum) to dryness. The resulting oily residue was purified by silica gel chromatography (15% MeOH/CHCl$_3$) to yield the title compound (160 mg, 33%) as a pale yellow solid: $^1$H NMR (400 MHz, DMSO-d$_6$) δ]8.67 (t, 1H), 8.19(d, 2H), 7.93 (d, 1H), 7.88 (s, 1H), 7.59–7.53 (dd, 2H0, 6.85 (d, 2H), 3.46–1.21 (m, 21H).

b) N-[4-(4-pyridyl)piperazinyl]isophthalyl-beta-alanine

Following the procedure of Example 1(d), the compound of Example 5 (a) was treated with 4 M HCl/dioxane to yield the title compound (40 mg, 29%): HPLC k' 4.46 (Ultrasphere ® ODS, gradient, A:acetonitrile B:water-0.1% trifluoroacetic acid, 5–60% acetonitrile during 20 min; UV detection at 220 nm). $^1$H NMR (400 MHz, DMSO-d$_6$) δ 8.66 (t, 1H), 8.19 (d, 2H), 7.93 (d, 1H), 7.89 (s, 1H), 7.59–7.53 (dd, 2H), 6.85 (d, 2H), 3.75–3.44 (m, 12H); MS (ES) m/e 383.2 [M+H]$^+$.

EXAMPLE 6

Preparation of N-{[Bis-4-(pyridyl)ethyl] amino}terephthalyl-beta-analine hydrochloride a) N-(methylterephthalyl)-beta-alanine-t-butyl ester EDC (11.43 g, 59.6 mmol) was added to a solution of monomethyl terephthalate (10.74 g, 59.6 mmol), tert-butyl-β-alanine hydrochloride (9.85 g, 54.2 mmol), HOBt. $H_2O$ (8.06 g, 59.6 mmol) and diisopropylethylamine (20.8 mL, 119.24 mmol) in anhydrous DMF (50 mL) at RT. After stirring for 20 h, the reaction was concentrated on the rotavap (high vacuum). The resulting residue was taken into EtOAc and washed sequentially with $H_2O$ (3×100 mL), 5% citric acid (3×100 ml), $H_2O$ (3×100 mL) and 10% $Na_2CO_3$ (2×100 mL). The organic extract was dried (anhydrous MgSO$_4$), concentrated and purified on silica gel chromatography (1% MeOH/CH$_2$Cl$_2$) to yield the title compound (14.79 g, 88.4%) as a white solid: $^1$H NMR (400 MHz, DMSO-d$_6$) δ 8.56 (t, 1H), 7.95 (s, 1H), 7.59 (s, 1H), 7.56 (d, 1H), 7.43 (d, 1H), 7.33 (d, 1H), 7.01 (t, 1H), 6.93 (t, 1H), 6.55 (d, 1H), 6.33 (br, 1H), 6.25 (s, 1H), 5.49 (d, 1H), 5.14 (t, 1H), 4.56 (d, 2H), 3.82 (d, 1H), 3.61 (s, 3H), 2.92 (s, 3H), 2.75 (dd, 1H), 2.53 (d, 1H). MS(ES) m/e 421.2 [M+H]$^+$.

b) N-(carboxyterephthalyl)-beta-alanine-t-butyl ester

Following the procedure of Example 1 (b), the compound of Example 6 (a) was saponified to give the title compound as a white solid: $^1$H NMR (400 MHz, DMSO-d$_6$) δ 8.55 (t, 1H), 7.57 (s, 1H), 7.56 (d, 1H), 7.43 (d, 1H), 7.33 (d, 1H), 7.01 (t, 1H), 6.93 (t, 1H), 6.55 (d, 1H), 6.33 (br, 1H), 6.25 (s, 1H), 5.49 (d, 1H), 5.08 (t, 1H), 4.55 (d, 2H), 3.82 (d, 1H), 2.92 (s, 3H), 2.75 (dd, 1H), 2.53 (d, 1H. MS (ES) m/e 407.2 [M+H]$^+$.

c) N-[[Bis-4-(pyridyl)ethyl]amino]terephthalyl-beta-alanine-t-butylester

Following the procedure of Example 1 (c), EDC (844 mg, 4.4 mmol) was added to the compound of Example 6 (b) (1.29 g, 4.0 mmol), Bis-4-pyridyl ethyl amine (908 mg, 4.0 mmol), HOBt. $H_2O$ (595 m g, 4.4 mmol) and diisopropylethylamine (0.84 mL, 4.8 mmol) in anhydrous DMF (10 mL) at RT. After stirring for 20 h, the reaction was concentrated on the rotavap (high vacuum). The resulting residue was taken into EtOAc and washed with $H_2O$ (3×20 mL), and saturated NaCl. The organic extract was dried (anhydrous MgSO$_4$), concentrated and purified on silica gel chromatography (1% MeOH/CH$_2$Cl$_2$) to yield the title compound (1.3 g, 65%) as a white solid. $^1$H NMR (400 MHz, CDCl$_3$) δ 8.57 (d, 2H), 8.44 (d, 2H), 7.74 (d, 2H), 7.13 (d, 2H), 6.99 (d, 2H), 6.80 (d, 2H), 3.79–1.46 (m, 21H).

d) N-[[Bis-4-(pyridyl)ethyl]amino]terephthalyl-beta-alanine

Following the procedure of Example 1 (d), 4 M HCl/dioxane (15 ml, 60 mmol) was added dropwise to a solution of the Example 6 (c) (600 mg, 1.19 mmol) in CH$_2$Cl$_2$ (15 ml) at Rt. The resulting mixture was stirred for 22 H. The resulting white precipitate was collected by filtration to yield the title compound (380 mg, 72%) as an off white solid. HPLC k' 4.21 (Ultrasphere ® ODS, gradient, A:acetonitrile B:water-0.1% trifluoroacetic acid, 5–60% acetonitrile during 20 min; UV detection at 220 nm). H NMR (400 MHz, DMSO-d$_6$) δ 8.87 (d, 2H), 8.77 (d, 2H), 8.70 (d, 1H), 8.09 (d, 1H), 7.82 (d, 1H), 7.16 (d, 2H), 3.90 (t, 2H), 3.56 (t, 2H), 3.47 (t, 2H), 3.45 (t, 2H), 3.28 (t, 2H), 3.12 (t, 2H). MS (ES) m/e 447.2 [M+H]$^+$. Anal. ($C_{25}H_{26}N_4O_4 \cdot 3$ HCl. $H_2O$) calcd: C, 52.30; H, 5.44; N, 9.76. Found: C, 52.25; H, 5.56; N, 9.78.

EXAMPLE 7

Preparation of N-[(tert-butoxycarbonyl)-4,4'-bipiperidinyl]terephthalyl-beta-alanine-tert-butylester Following the procedure of Example 1 (c), a mixture containing the compound of Example 6 (b) (879 mg, 3.0 mmol), EDC (690 mg, 3.6 mmol), HOBt. $H_2O$ (446 m g, 3.3 mmol), N-(tert-butoxycarbonyl)-4,4'-bipiperidine (805 mg, 3 mmol), and diisopropylethylamine (0.63 mL, 3.6 mmol) in anhydrous DMF (5 mL) was stirred at RT for 20 h. The reaction mixture was concentrated on the rotavap (high vacuum) to dryness. The resulting residue was take into EtOAc and washed sequentially with $H_2O$ (3×20 mL), 5% citric acid (3×20 ml), $H_2O$, 10% $Na_2CO_3$ (3×20 ml) and saturated NaCl. The organic extract was dried (anhydrous MgSO$_4$), filtered and concentration. the resulting residue was chromatographed on silica gel (1% MeOH/CH$_2$Cl$_2$) to yield the title compound (530 mg, 33%) as a white solid. $^1$H NMR (400 MHz, CDCl$_3$) δ (7.79 (d, 2H), 7.44 (d, 2H), 3.70–1.43 (m, 40H).

b) N-[4,4'-Bipiperidin-1-yl]terephthalyl-beta-alanine

Following the procedure of Example 1 (d), the compound of Example 7 (a) (530 mg, 0.98 mmol) was stirred with 4 M HCl/dioxane (12 ml, 48 mmol) in CH$_2$Cl$_2$ (12 ml) at RT for 22 h. The resulting white precipitate was collected by filtration to yield the title compound (270 mg, 72%) as white solid. HPLC k' 4.68 (Ultrasphere ® ODS, gradient, A:acetonitrile B:water-0.1% trifluoroacetic acid, 5–60% acetonitrile during 20 min; UV detection at 220 nm). $^1$H NMR (400 MHz, DSMO-d$_6$) δ 7.87 (d, 2H), 7.43 (d, 2H), 3.71–1.36 (m, 22H). MS (ES) m/e 388.2 [M+H]$^+$. Anal. ($C_{21}H_{29}N_3O_4 \cdot 1.5$ HCl. 1 $H_2O$) calcd: C, 54.81; H, 7.12; N, 9.13. Found: C, 54.68; H, 7.16; N, 9.04.

EXAMPLE 8

Preparation of N-[4,4'-Bipiperidin-1-yl]isophthalyl-4-aminobutyric acid a) Ethyl N-[(tert-butoxycarbonyl)-4,4'-bipiperidinyl]isophthalyl-4-aminobutyrate EDC (263 mg, 1.37 mmol) was added to a solution of the compound of Example 4 (b) (570 mg, 1.37 mmol), ethyl-4-aminobutyrate hydrochloride (230 mg, 1.37 mmol), HOBt. $H_2O$ (190 mg, 1.37 mmol) and DIEA (480 µL, 2.75 mmol) in anhydrous DMF (7 mL) at RT. After stirring for 20 h, the reaction was concentrated on rotavap (high vacuum). The resulting residue was taken into EtOAc and washed successively with $H_2O$ (3×20 mL), 5% citric acid (3×20 ml), $H_2O$, 10% $Na_2CO_3$ (3×20 ml) and saturated NaCl. The organic extract was dried (anhydrous $Na_2SO_4$), filtered and concentrated to yield the title compound (670 m g, 92%) as a white solid. HPLC k' 11.8 (Ultrasphere ® ODS, gradient, A:acetonitrile B:water-0.1% trifluoroacetic acid, 5–60% acetonitrile during 20 min; UV detection at 220 nm). MS (ES) m/e 530.2 [M+H]⁺.

b) Ethyl N-[4,4'-Bipiperidin-1-yl]isophthalyl-4-aminobutyrate

To a solution of the compound of Example 8 (a) (670 mg, 1.26 mmol) in $CH_2Cl_2$ (8 ml) was added trifluoroacetic acid (TFA) (2 ml). The resulting mixture was stirred for 2 h, then it was concentrated to dryness on rotavap.

c) N-[4,4'-Bipiperidin-1-yl]isophthalyl-4-piperidine carboxylic acid

To a solution of the compound of Example 8 (b) in ethanol (10 mL) was added a solution of 1N NaOH (6.3 mL, 6.3 mmol) and stirred at RT for 20 h. It was then concentrated, and the resulting oily residue was dissolved in $H_2O$, and the pH was adjusted to 7 by means of 50% acetic acid. The aqueous solution was purified on flash ODS column (step gradient, 2–9% acetonitrile/water. The fractions containing the pure compound were collected, concentrated and lyophilized to yield the title compound (350 mg, 70%) as a white powder. HPLC k' 5.38 (Ultrasphere ® ODS, gradient, A:acetonitrile B:water-0.1% trifluoroacetic acid, 5–60% acetonitrile during 20 min; UV detection at 220 nm). MS (ES) m/e 430.4 [M+H]⁺; Anal. ($C_{22}H_{31}N_3O_4$ . 2.0 $H_2O$) calcd: C, 60.39; H, 8.06; N, 9.60. Found: C, 60.49; H, 8.05; N, 9.50.

EXAMPLE 9

Preparation of N-[[Bis-4-(piperidinyl)ethyl]amino]terephthalyl-beta-alanine hydrochloride a) N-[[Bis-4-(piperidinyl)ethyl]amino]terephthalyl-beta-alanine-t-butylester Following the procedure of Example 3 (a), the compound 6 (c) was hydrogenated at 50 psi in a Parr apparatus at RT for 5 h. The reaction mixture was purged with argon, filtered and concentrated to yield the title compound as pale yellow solid. ¹H NMR (400 MHz, DMSO-$d_6$) δ 7.88 (d, 2H), 7.45 (d, 2H), 3.45–1.39 (m, 40H); MS (ES) m/e 515.4 [M+H]⁺.

b) N-[[Bis-4-(piperidinyl)ethyl]amino]terephthalyl-beta-alanine

Following the procedure of 3 (b), the compound of Example 9 (a) was treated with a solution of 4 M HCl/dioxane to yield the title compound. HPLC k' 5.95 (Ultrasphere ® ODS, gradient, A:acetonitrile B:water-0.1% trifluoroacetic acid, 5–60% acetonitrile during 20 min; UV detection at 220 nm). ¹H NMR (400 MHz, DMSO-$d_6$) δ 7.86 (d, 2H), 7.42 (d, 2H), 3.44–1.23 (m, 32H). MS (ES) m/e 459.2[M+H]⁺. Anal. ($C_{25}H_{38}N_4O_4$ . 0.5 HCl. 2.25 $H_2O$) calcd: C, 58.04; H, 8.38; N, 10.83. Found: C, 57.96; H, 8.35; N, 10.53.

EXAMPLE 10

Preparation of N-[4-(4-Pyridyl)piperazinyl]terephthalyl-beta-alanine

Following the procedure of Example 1, the title compound was prepared.

The examples which follow are intended to in no way limit the scope of this invention, but are provided to illustrate how to make and use the compounds of this invention. Many other embodiments will be readily apparent and available to those skilled in the art.

What is claimed is:

1. A compound of the formula:

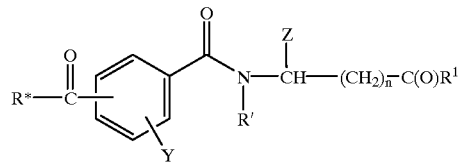

wherein:
R* is

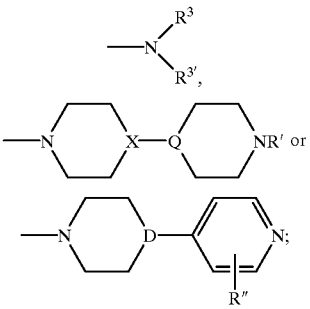

$R^1$ is OR' or NR'R';

each R' independently is hydrogen or $C_{1-6}$alkyl;

R" is hydrogen, $C_{1-6}$alkyl, or NR'R';

X and Q independently are CH or N, with the proviso that X and Q are not simultaneously N;

D is CH or N, with the proviso that when D is N, R" is NR'R';

Y is hydrogen, $C_{1-6}$alkyl, halo, $CF_3CH_2OR^2$, $COR^2$, $CONR^2R^2$, $CO_2R^2$, CN, aryl, heteroaryl, $NR^2R^2$, $NR^2COR^2$, $NR^2CO_2R^2$, $NR^2CONR^2R^2$, $NR^2SO_2R^2$, $NO_2$, $OR^2$, $S(O)_{0-2}R^2$, or $SO_{(0-2)}CF_3$;

Z is hydrogen, $C_{1-6}$alkyl, $CH_2OR^2$, $CH_2CO_2R^2$, $C_{2-6}$alkenyl, $C_{2-6}$alkynyl, aryl, aralkyl$C_{1-6}$, heteroaryl, heteroaralkyl$C_{1-6}$, $COR^2$, $CONR^2R^2$, $CO_2R^2$, $NR^2R^2$, $NR^2COR^2$, $NR^2CONR^2R^2$, $NR^2CO_2R^2$, $NR^2SO_2R^2$, $OR^2$, $SO_2R^2$, or $SO_2NR^2R^2$;

$R^2$ is hydrogen, $C_{1-6}$alkyl, aralkyl$C_{1-6}$, aryl, heteroaralkyl$C_{1-6}$, or heteroaryl;

$R^3$ and $R^{3'}$ independently are —$(CH_2)_s$—Ⓝ;

Ⓝ is piperidine, piperazine, or 2-, 3-, or 4-pyridine;

s is 1–4; and n is 0–3;

or a pharmaceutically acceptable salt thereof.

2. A compound according to claim 1 of the formula:

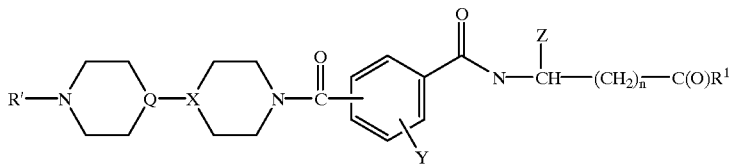

wherein:

$R^1$ is OR' or NR'R';

each R' independently is hydrogen or $C_{1-6}$alkyl;

X and Q independently are CH or N, with the proviso that X and Q are not simultaneously N;

Y is hydrogen, $C_{1-6}$alkyl, halo, $CF_3$, $CH_2OR^2$, $COR^2$, $CONR^2R^2$, $CO_2R^2$, CN, aryl, heteroaryl, $NR^2R^2$, $NR^2COR^2$, $NR^2CO_2R^2$, $NR^2CONR^2R^2$, $NR^2SO_2R^2$, $NO_2$, $OR^2$, $S(O)_{0-2}R^2$, or $SO_{(0-2)}CH_3$;

Z is hydrogen, $C_{1-6}$alkyl, $CH_2OR^2$, $CH_2CO_2R^2$, $C_{2-6}$alkenyl, $C_{2-6}$alkynyl, aryl, aralkyl$C_{1-6}$, heteroaryl, heteroaralkyl$C_{1-6}$, $COR^2$, $CONR^2R^2$, $CO_2R^2$, $NR^2R^2$, $NR^2COR^2$, $NR^2CONR^2R^2$, $NR^2CO_2R^2$, $NR^2SO_2R^2$, $OR^2$, $SO_2R^2$, or $SO_2NR^2R^2$;

$R^2$ is hydrogen, $C_{1-6}$alkyl, aralkyl$C_{1-6}$, aryl, heteroaralkyl$C_{1-6}$, or heteroaryl, and;

n is 0–3;

or a pharmaceutically acceptable salt thereof.

3. A compound according to claim 2 wherein Z is hydrogen, $C_{1-6}$alkyl, $CH_2OR^2$, $CH_2CO_2R^2$, $COR^2$, $CONR^2R^2$, $CO_2R^2$, $NR^2R^2$, or $OR^2$.

4. A compound according to claim 3 wherein $R^1$ is OR' and X and Q are each CH.

5. A compound according to claim 4 which is:

N-[4,4'-bipiperidin-1-yl]isophthalyl-beta-alanine;

N-[4,4'-bipiperidin-1-yl]isophthalylglycine;

N-[4,4'-bipiperidin-1-yl]isophthalyl-4-aminobutyric acid; or

N-[4,4'-bipiperidin-1-yl]terephthalyl-beta-alanine;

or a pharmaceutically acceptable salt thereof.

6. A compound according to claim 1 of the formula:

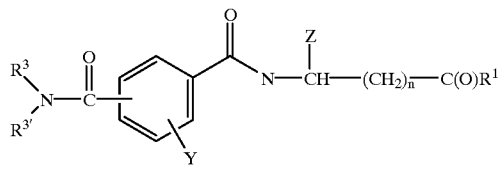

wherein:

$R^1$ is OR' or NR'R';

each independently is hydrogen or $C_{1-6}$alkyl;

Y is hydrogen, $C_{1-6}$alkyl, halo, $CF_3$, $CH_2OR^2$, $COR^2$, $CONR^2R^2$, $CO_2R^2$, CN, aryl, heteroaryl, $NR^2R^2$, $NR^2COR^2$, $NR^2CO_2R^2$, $NR^2CONR^2R^2$, $NR^2SO_2R^2$, $NO_2$, $OR^2$, $S(O)_{0-2}R^2$, or $SO_{(0-2)}CF_3$;

Z is hydrogen, $C_{1-6}$alkyl, $CH_2OR^2$, $CH_2CO_2R^2$, $C_{2-6}$alkenyl, $C_{2-6}$alkynyl, aryl, aralkyl$C_{1-6}$, heteroaryl, heteroaralkyl$C_{1-6}$, $COR^2$, $CONR^2R^2$, $CO_2R^2$, $NR^2R^2$, $NR^2COR^2$, $NR^2CONR^2R^2$, $NR^2CO_2R^2$, $NR^2SO_2R^2$, $OR^2$, $SO_2R^2$, or $SO_2NR^2R^2$;

$R^2$ is hydrogen, $C_{1-6}$alkyl, aralkyl$C_{1-6}$, aryl, heteroaralkyl$C_{1-6}$, or heteroaryl;

$R^3$ and $R^{3'}$ independently are $—(CH_2)_s—\text{\textcircled{N}}$;

\textcircled{N} is piperidine, piperazine, or 2-, 3-, or 4-pyridine;

s is 1–4; and n is 0–3;

or a pharmaceutically acceptable salt thereof.

7. A compound according to claim 6 wherein Z is hydrogen, $C_{1-6}$alkyl, $CH_2OR^2$, $CH_2CO_2R^2$, $COR^2$, $CONR^2R^2$, $CO_2R^2$, $NR^2R^2$, or $OR^2$.

8. A compound according to claim 7 wherein $R^1$ is OR'.

9. A compound according to claim 8 which is:

N-[[bis-4-(pyridyl)ethyl]amino]isophthalyl-beta-alanine;

N-{[bis-4-(piperidinyl)ethyl]amino}isophthalyl-beta-alanine;

N-{[bis-4-(pyridyl)ethyl]amino}terephthalyl-beta-alanine; or

N-[[bis-4-(piperidinyl)ethyl]amino]terephthalyl-beta-alanine;

or a pharmaceutically acceptable salt thereof.

10. A compound according to claim 1 of the formula:

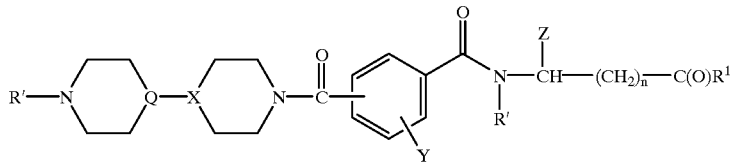

wherein:

$R^1$ is OR' or NR'R';

each R' independently is hydrogen or $C_{1-6}$alkyl;

R" is hydrogen, $C_{1-6}$alkyl, or NR'R';

X is CH or N;

Y is hydrogen, $C_{1-6}$alkyl, halo, $CF_3$, $CH_2OR^2COR^2$, $CONR^2R^2$, $CO_2R^2$, CN, aryl, heteroaryl, $NR^2R^2$, $NR^2COR^2$, $NR^2CO_2R^2$, $NR^2CONR^2R^2$, $NR^2SO_2R^2$, $NO_2$, $OR^2$, $S(O)_{0-2}R^2$, or $SO_{(0-2)}CF_3$;

Z is hydrogen, $C_{1-6}$alkyl, $CH_2OR^2$, $CH_2CO_2R^2$, $C_{2-6}$alkenyl, $C_{2-6}$alkynyl, aryl, aralkyl$C_{1-6}$, heteroaryl, heteroaralkyl$C_{1-6}$, $COR^2$, $CONR^2R^2$, $CO_2R^2$, $NR^2R^2$, $NR^2COR^2$, $NR^2CONR^2R^2$, $NR^2CO_2R^2$, $NR^2SO_2R^2$, $OR^2$, $SO_2R^2$, or $SO_2NR^2R^2$;

$R^2$ is hydrogen, $C_{1-6}$alkyl, aralkyl$C_{1-6}$, aryl, heteroaralkyl$C_{1-6}$, or heteroaryl and;

n is 0–3;

or a pharmaceutically acceptable salt thereof.

11. A compound according to claim 10 wherein Z is hydrogen, $C_{1-6}$alkyl, $CH_2OR^2$, $CH_2CO_2R^2$, $COR^2$, $CONR^2R^2$, $CO_2R^2$, $NR^2R^2$, or $OR^2$.

12. A compound according to claim 11 wherein $R^1$ is OR' and X is N.

13. A compound according to claim 12 which is:

N-[4-(4-pyridyl)piperazinyl]isophthalyl-beta-alanine; or

N-[4-(4-pyridyl)piperazinyl]terphthalyl-beta-alanine;

or a pharmaceutically acceptable salt thereof.

14. A pharmaceutical composition comprising a compound according to claim 1 and a pharmaceutically acceptable carrier.

15. A method for effecting inhibition of platelet aggregation which comprises administering a compound according to claim 1.

16. A method for treating stroke or a transient ischemia attack or myocardial infarction which comprises administering a compound according to claim 1.

17. A method for promoting reperfusion of an artery or vein and inhibiting reocclusion which comprises administering a fibrinolytic agent and a compound according to claim 1.

* * * * *